United States Patent [19]

Yonemura et al.

[11] Patent Number: 5,792,855
[45] Date of Patent: Aug. 11, 1998

[54] WATER-ABSORBENT RESINS AND MANUFACTURING METHODS THEREOF

[75] Inventors: Koichi Yonemura; Kazuhisa Hitomi, both of Himeji; Akiko Mitsuhashi, Sanda; Takaya Hayashi, Tsuchiura; Nobuyuki Harada, Suita, all of Japan

[73] Assignee: Nippon Shokubai Co., Ltd., Osaka, Japan

[21] Appl. No.: 788,201

[22] Filed: Jan. 24, 1997

Related U.S. Application Data

[63] Continuation of Ser. No. 283,855, Aug. 1, 1994, abandoned.

[30] Foreign Application Priority Data

Aug. 3, 1993 [JP] Japan ............ 5-192424

[51] Int. Cl.$^6$ ............ C08B 16/00
[52] U.S. Cl. ............ 536/56; 536/58; 536/63
[58] Field of Search ............ 536/56, 58, 63

[56] References Cited

U.S. PATENT DOCUMENTS

| | | | |
|---|---|---|---|
| 4,697,008 | 9/1987 | Asano et al. | 536/89 |
| 4,722,739 | 2/1988 | Blanchard et al. | 8/597 |
| 4,990,551 | 2/1991 | Häubl et al. | 524/30 |

FOREIGN PATENT DOCUMENTS

| | | |
|---|---|---|
| A-0366968 | 5/1990 | European Pat. Off. |
| 0 426 368 A2 | 5/1991 | European Pat. Off. |
| 0 527 271 A1 | 2/1993 | European Pat. Off. |
| 0 538 904 A2 | 4/1993 | European Pat. Off. |
| 0 566 118 A1 | 10/1993 | European Pat. Off. |
| A-2591601 | 6/1987 | France. |
| 49-128987 A | 12/1974 | Japan. |
| 50-5312 A | 1/1975 | Japan. |
| 50-85689 A | 7/1975 | Japan. |
| 54-163981 A | 12/1979 | Japan. |
| 55-500785 A | 10/1980 | Japan. |
| 56-5137 A | 1/1981 | Japan. |
| 56-28755 A | 3/1981 | Japan. |
| 56-76419 A | 6/1981 | Japan. |
| 57-137301 A | 8/1982 | Japan. |
| 58-1701 A | 1/1983 | Japan. |
| 60-58443 A | 4/1985 | Japan. |
| 61-89364 A | 5/1986 | Japan. |
| 4-161431 A | 6/1992 | Japan. |
| 5-49925 A | 3/1993 | Japan. |
| 5-123573 | 5/1993 | Japan. |
| 5-123573 A | 5/1993 | Japan. |
| WO 92/20349 | 11/1992 | WIPO. |

*Primary Examiner*—Bernard Lipman
*Attorney, Agent, or Firm*—Kubovick & Kubovcik

[57] ABSTRACT

Water-absorbent resins which are prepared by mixing polysaccharides with amino acids (amino acids and/or polymers of amino acids) and heating the mixture so as to cause a crosslinking reaction therein. Each of the water-absorbent resins has a water-absorbing ratio of not less than 10 g/g with respect to physiologic saline as well as having a rate of biodegradability of not less than 10%. Moreover, its water-absorbing ratio under pressure is not less than 10 ml/g with respect to physiologic saline. The water-absorbing ratio under pressure is measured by using a measuring device that is constituted of a weighing machine, a container, an air-intake pipe, a conduit, a glass filter, and a measuring section. The water-absorbent resins are superior in both water-absorbing capacity and biodegradability, and are capable of maintain their water-absorbing capacity even under pressure.

8 Claims, 2 Drawing Sheets

WATER-ABSORBENT RESINS AND MANUFACTURING METHODS THEREOF

This application is a continuation of application Ser. No. 08/283,855 filed Aug. 1, 1994 now abandoned.

FIELD OF THE INVENTION

The present invention relates to water-absorbent resins which have a superior water-absorbing capacity for aqueous fluids as well as having excellent biodegradability, and also concerns manufacturing methods thereof.

BACKGROUND OF THE INVENTION

Recently, water-absorbent resins have been used not only for paper diapers and sanitary napkins, but also for a wide variety of products in various fields, such as absorbent materials for body fluids in the medical field; sealing materials (water-sealing materials) and anti-dewing materials in the engineering and building fields; freshness-retaining materials in the food field; dehydrating agents for removing water from solvents in the industrial field; and materials related to tree-planting in the gardening and agricultural fields. Thus, various water-absorbent resins have been proposed in order to meet each of these demands.

Among these water-absorbent resins that have been proposed, chemical compounds of polyacrylic acids (salts) are generally used extensively, since they are inexpensive and have a superior water-absorbing capacity. However, the water-absorbent resins of polyacrylic acids (salts) have hardly any biodegradability although they do have slight photo-degradability in the water-absorbed state. Therefore, upon being disposed as wastes, even if those water-absorbent resins are buried in the ground, they are not decomposed by bacteria and microbes in the ground; this results in environment hygiene problems such as environmental pollution. In other words, the disadvantage of the water-absorbent resins of polyacrylic acids (salts) is that they are difficult materials to dispose.

In general, pulp, paper and other materials made of starch, carboxymethylcellulose salts, or cellulose have been known as water-absorbent products that are biodegradable. However, these water-absorbent products depend on a capillary action or a thickening property in absorbing water. Consequently, the water-absorbent products are inferior in their gel strength under pressure; thus, upon receipt of an external pressure, their water-absorbing capacity is lowered, thereby causing the water that has been once absorbed to be released.

In order to solve these problems, conventionally, various water-absorbent resins, which are prepared by graft-polymerizing or crosslinking polysaccharides, have been used as water-absorbent resins which have a superior water-absorbing capacity as well as having excellent biodegradability. The manufacturing methods for the above-mentioned water-absorbent resins include, for example, a method wherein a hydrophilic monomer is graft-polymerized to polysaccharides (Japanese Laid-Open Patent Publication No. 76419/1981(Tokukaishou 56-76419)) and a method wherein polysaccharides themselves are crosslinked (Japanese Laid-Open Patent Publications No. 5137/1981 (Tokukaishou 56-5137) and No. 58443/1985 (Tokukaishou 60-58443)). Moreover, another method has been proposed wherein cellulose derivatives are used as polysaccharides and these cellulose derivatives are crosslinked (Japanese Laid-Open Patent Publications No. 128987/1974 (Tokukaishou 49-128987), No. 85689/1975 (Tokukaishou 50-85689), No. 163981/1979 (Tokukaishou 54-163981), No. 28755/1981(Tokukaishou 56-28755), No. 137301/1982 (Tokukaishou 57-137301), No. 1701/1983 (Tokukaishou 58-1701), No. 89364/1986(Tokukaishou 61-89364), No. 161431/1992 (Tokukaihei 4-161431), No. 49925/1993 (Tokukaihei 5-49925), and No. 123573/1993 (Tokukaihei 5-123573), as well as Japanese Examined Patent Publication No. 500785/1980 (Tokukoushou 55-500785)).

However, the above-mentioned conventional water-absorbent resins, that is, the water-absorbent resins that are obtained by graft-polymerizing or crosslinking polysaccharides such as cellulose derivatives, are inferior in their biodegradability to the polysaccharides that are their parent materials. In other words, the above-mentioned conventional water-absorbent resins are inferior in their biodegradability. Moreover, even if provisions are made so that the polysaccharides are graft-polymerized or crosslinked while maintaining the biodegradability that is inherent in the polysaccharides, the water-absorbing capacity of the resulting water-absorbent resins is extremely lowered. Consequently, one of the disadvantages of the conventional water-absorbent resins is that either the water-absorbing capacity or the biodegradability is lowered, and that it is impossible to obtain performance that satisfies both of the factors.

For this reason, it has been expected to develop water-absorbent resins which are superior in both their water-absorbing capacity and biodegradability, and manufacturing methods thereof.

SUMMARY OF THE INVENTION

It is an object of the present invention to provide water-absorbent resins which are superior in both their water-absorbing capacity and biodegradability and are capable of maintaining their water-absorbing capacity even under pressure, as well as providing manufacturing methods thereof.

After having earnestly studied to develop water-absorbent resins which are superior in both their water-absorbing capacity and biodegradability as well as the manufacturing methods thereof, the inventors and other related personnel of the present invention have discovered that water-absorbent resins, which are obtained by mixing polysaccharides with amino-acids and heating the mixture, have excellent performances that the other conventional water-absorbent resins have never attained. Further, the inventors and other related personnel have discovered that, in the case of using carboxyalkyl-cellulose alkaline metallic salts as polysaccharides, water-absorbent resins prepared through the following processes have excellent performances that the other conventional water-absorbent resins have never attained. In the processes, a mixture, which is prepared by dissolving the polysaccharides and polycarboxylic acids in a solvent, is heated, and the resulting product, obtained after removing the solvent from the mixture, is heated to form corresponding crosslinked polymer. Then, aqueous gel of the crosslinked polymer is formed, and the water in the aqueous gel is replaced by a hydrophilic organic solvent, thereby producing the water-absorbent resins.

In order to achieve the above-mentioned object, water-absorbent resins in accordance with the present invention are characterized in that they are prepared by having polysaccharides closslinked by amino acids.

Further, other water-absorbent resins in accordance with the present invention are characterized in that they are prepared by having polysaccharides closslinked by polycarboxylic acids.

Moreover, still other water-absorbent resins in accordance with the present invention are characterized in that they have a water-absorbing ratio of not less than 10 g/g with respect to physiologic saline, as well as having a rate of biodegradability of not less than 10%.

In the above arrangement, the water-absorbent resins are formed by crosslinking polysaccharides with amino acids or polycarboxylic acids. The water-absorbent resins have a water-absorbing ratio of not less than 10 g/g with respect to physiologic saline, as well as having a rate of biodegradability of not less than 10%. Therefore, the water-absorbent resins are superior in both their water-absorbing capacity and biodegradability, and are capable of maintaining their water-absorbing capacity even under pressure. The water-absorbent resins are used not only for sanitary materials such as paper diapers and sanitary napkins in the sanitary field, but also for various products in various fields, such as the medical field; the engineering and building fields; the food field; the industrial field; and the gardening and agricultural fields. They are also used for various other products, such as oil-water separating materials, waste-liquid absorbing materials, vibration-proof materials, sound-proof materials, general merchandise for home use, toys, and artificial snow.

Further, in order to achieve the above-mentioned object, a manufacturing method for the water-absorbent resins of the present invention is characterized in that polysaccharides are mixed with amino acids and heated.

Moreover, another manufacturing method for the water-absorbent resins of the present invention is characterized in that: polysaccharides are mixed with amino acids; the mixture is heated and the resulting product is formed into an aqueous gel; and water in the aqueous gel is replaced by a hydrophilic organic solvent.

Furthermore, still another manufacturing method for the water-absorbent resins of the present invention is characterized in that: a mixture, which is prepared by dissolving carboxyalkylcellulose alkaline metallic salts as polysaccharides and polycarboxylic acids in a solvent, is heated and the resulting product, obtained after removing the solvent from the mixture, is heated to form a corresponding crosslinked polymer; an aqueous gel of the crosslinked polymer is formed; and the water in the aqueous gel is replaced by a hydrophilic organic solvent.

In the above-mentioned methods, by crosslinking polysaccharides with amino acids or polycarboxylic acids, it is possible to produce water-absorbent resins which exhibit superior performances as described earlier.

For a fuller understanding of the nature and advantages of the invention, reference should be made to the ensuing detailed description taken in conjunction with the accompanying drawings.

The following description will discuss the present invention in detail.

Polysaccharides to be used as raw materials in the present invention, which are not intended to be limited to any specific materials, include polysaccharides, derivatives of polysaccharides, and salts thereof.

Specific examples of the polysaccharides include cellulose, methylcellulose, ethylcellulose, methylethylcellulose, hemicellulose, starch, methylstarch, ethylstarch, methylethylstarch, agar-agar, carrageenan, alginic acid, pectic acid, cyamoposis gum, tamarind gum, locust bean gum, devil's-tongue (konnyaku) mannan, dextran, xanthan gum, pullulan, gellan gum, chitin, chitosan, chondroitin sulfide, heparin, and hyaluronic acid.

The derivatives of polysaccharides, which are formed through carboxymethylation or hydroxyalkylation of the polysaccharides, for example, include carboxymethylcellulose, hydroxyethylcellulose, starch-glycolic acid, derivatives of agar-agar, and derivatives of carrageenan.

These polysaccharides may be used as a single material, or may be used as mixed materials in two or more kinds, as occasion demands. Among these polysaccharides, it is preferable to employ carboxyalkylcellulose, carboxyalkylstarch and salts thereof. Here, as to the salts, it is preferable to employ alkaline metallic salts such as sodium salts and potassium salts.

The above-mentioned alkaline metallic salts of carboxyalkylates of polysaccharides are obtained as follows: for example, wood pulp such as conifer pulp, linter pulp, and other materials that contain cellulose are reacted with an etherifying agent, such as a chloracetic acid, and alkaline metal hydroxides in a water-containing hydrophilic organic solvent. The degree of etherification of the alkaline salts of polysaccharides is set to fall within the range of 0.2–1.0, preferably within the range of 0.3–0.6.

As to the amino acids for use in a crosslinking process of polysaccharides in the present invention, at least one kind, which is selected from the group consisting of amino acid and amino-acid polymers, is employed. In other words, the water-absorbent resins are formed by making the polysaccharides crosslinked by amino acid and/or amino-acid polymers.

The above-mentioned amino acids, which are not especially limited as long as they are reactive with the hydroxy groups and carboxyl groups of the polysaccharides, for example, include glycine, alanine, valine, leucine, isoleucine, phenylalanine, proline, serine, threonine, tyrosine, cysteine, cystine, methionine, tryptophane, lysin, arginine, histidine, and acidic amino acids such as aspartic acid and glutamic acid, and salts thereof. These amino acids may be used as a single material, or may be used as mixed materials in two or more kinds, as occasion demands. Among these amino acids, it is preferable to employ acidic amino acids such as aspartic acid and glutamic acid, and salts thereof. Here, as to the salts, it is preferable to employ alkaline metallic salts such as sodium salts and potassium salts.

Further, the above-mentioned amino-acid polymers, which are not especially limited as long as they are reactive with the hydroxy groups and carboxyl groups of the polysaccharides, more specifically, include polymers of the amino acids exemplified above, and the salts, etc. thereof. These amino-acid polymers may be used as a single material, or may be used as mixed materials in two or more kinds, as occasion demands. Among these amino-acid polymers, it is preferable to employ acidic polyamino acids, such as polyaspartic acid, polyglutamic acid, and copolymers of aspartic acid and glutamic acid, and salts thereof. Here, as to the salts, it is preferable to employ alkaline metallic salts such as sodium salts and potassium salts.

Moreover, in the case of using amino acids and amino-acid polymers together at the same time, the combination and mixing rate are not especially limited, but are desirably set depending on the kinds of the polysaccharides.

The load of the amino acids in relation to the polysaccharides is not especially limited, but is desirably set depending on the kinds of the polysaccharides or the amino acids that are to be used. More specifically, for example, the load of the amino acids is within the range of 0.01 part to 30 parts by weight with respect to the polysaccharides of 100 parts by weight. Preferred is within the range of 0.1 part to 10 parts by weight, and the most preferred is within the range of 0.1 part to 5 parts by weight. It is not preferable to use the load of the amino acids less than 0.01 part by weight, because the resulting water-absorbent resins do not achieve desired levels in performances such as water-retaining capacity. Further, it is not preferable to use the load of the amino acids greater than 30 parts by weight, because the resulting water-absorbent resins become inferior in performances such as water-absorbing capacity and because the costs of production become high.

Moreover, in the present invention, in the case of using alkaline metallic salts of carboxyalkylcellulose as the polysaccharides, the polycarboxylic acids, which are used for crosslinking the polysaccharides, are not especially limited, as long as they have two or more carboxyl groups that are reactive with the hydroxy groups and carboxyl groups of the polysaccharides. Further, the polycarboxylic acids may have hydroxy groups. Specific examples of the polycarboxylic acids include malic acid, citrate, tartaric acid, polyacrylic acid, maleic acid, polymaleic acid, succinic acid, acid-type carboxymethylcellulose, and salts thereof. These polycarboxylic acids may be used as a single material, or may be used as mixed materials in two or more kinds, as occasion demands.

The load of the polycarboxylic acids in relation to the polysaccharides is not especially limited, but is desirably set depending on the kinds of the polysaccharides or the polycarboxylic acids that are to be used. More specifically, for example, the load of the polycarboxylic acids is within the range of 1 part to 100 parts by weight with respect to the polysaccharides of 100 parts by weight. Preferred is within the range of 30 parts to 80 parts by weight. It is not preferable to use the load of the polycarboxylic acids less than 1 part by weight, since the resulting water-absorbent resins do not achieve desired levels in performances such as water-retaining capacity. Further, it is not preferable to use the load of the polycarboxylic acids greater than 100 parts by weight, since the resulting water-absorbent resins become inferior in performances such as water-absorbing capacity and the costs of production become high.

The water-absorbent resins in accordance with the present invention are prepared by mixing the polysaccharides with the amino acids and heating the mixture, that is, by making the polysaccharides crosslinked by the amino acids. Also, the water-absorbent resins in accordance with the present invention are prepared by making the polysaccharides crosslinked by the polycarboxylic acids.

Upon making the polysaccharides crosslinked by the amino acids or the polyhydric carboxylic acids, it is preferable to mix both of the materials uniformly and sufficiently, in order to obtain a uniform crosslinking reaction. The mixing method of the polysaccharides and the amino acids or the polycarboxylic acids is not especially limited: examples of the method include a method wherein both of the materials in solid states are mixed (dry mixing method), a method wherein both of the materials in slurry states are mixed, a method wherein either of the materials is converted into a slurry state and the other is added and mixed thereto, a method wherein both of the materials in solution states are mixed, and a method wherein either of the materials is converted into a solution state and the other is added and mixed thereto. Among these mixing methods, it is preferable to employ the method wherein either of the materials is converted into a solution state and the other is added and mixed thereto.

In the above-mentioned mixing method, that is, in the manufacturing method for the water-absorbent resins, solvents are used, as occasion demands. In the case of using solvents, the following chemical compounds are preferably used: for example, water, or hydrophilic organic solvents that are uniformly mixed with water, such as lower alcohols like methyl alcohol, ethyl alcohol, propyl alcohol, isopropyl alcohol, and butyl alcohol. As to the hydrophilic organic solvents, those having comparatively low boiling points are preferably used. Additionally, in the case of using water and hydrophilic organic solvents combinedly as a solvent, the mixing rate of both of the materials may be desirably set by taking into consideration the kinds, solubilities, and other factors of the polysaccharides, amino acids and polycarboxylic acids. More specifically, for example, the load of the hydrophilic organic solvents is within the range of 300 parts to 2000 parts by weight in relation to water of 100 parts by weight. Further, the load of the solvent in the above-mentioned manufacturing method may be desirably set by taking into consideration the kinds, solubilities, and other factors of the polysaccharides, amino acids and polycarboxylic acids. Additionally, the hydrophilic organic solvents exemplified above may be preferably applied to cases where alkaline metallic salts of carboxyalkylates are obtained from the polysaccharides.

Among the mixing methods described above, in the case of using the solvent, it is preferable to employ the method wherein either of the materials is converted into a solution state and the other is added and mixed thereto: most preferred is the method wherein the water solution of the polysaccharides is prepared and the amino acids or polycarboxylic acids are added to and mixed with the solution.

In order to prepare the water solution of the polysaccharides, it is preferable to set the density of the water solution of the polysaccharides within the range of 0.1% to 20% by weight, more preferably within the range of 0.5 weight % to 10 weight %. If the density is lower than 0.1% by weight, a large quantity of the water solution is required, and in order to remove water therefrom, the water solution, for example, needs to be heated for a long time, causing the efficiency of the production to become low. Conversely, if the density is higher than 20% by weight, the viscosity of the water solution becomes higher; this makes it impossible to mix the water solvent, that is, the polysaccharides, with the amino acids or the polycarboxylic acids uniformly and sufficiently.

It is preferable to set the heating temperature within the range of 70° C. to 200° C., more preferably within the range of 110° C. to 180° C. Upon conducting the crosslinking reaction, it is not preferable to use heating temperatures lower than 70° C. because the crosslinking reaction hardly progresses. Also, it is not preferable to use heating temperatures higher than 200° C. because the polysaccharides decompose to be colored. Here, the heating method is not especially limited: for example, various methods, such as a method irradiating far infrared rays, a method irradiating microwaves, or methods wherein a hot-air dryer or a vacuum dryer is used, are adopted.

The heating time is not especially limited, and may be set desirably depending on the kinds and combinations of polysaccharides, amino acids, or polycarboxylic acids, and solvents, the heating temperature, the physical properties of desired water-absorbent resins, and other factors. More specifically, for example, in the case of using the heating temperature of 120° C., the heating time is set to be in the range of 1 minute to 5 hours, more preferably, in the range of 5 minutes to 200 minutes. Further, in the case of crosslinking the polysaccharides by using the polyhydric carboxylic acids, it is preferably set to be in the range of 30 minutes to 5 hours.

As to the manufacturing methods of the water-absorbent resins of the present invention, the following method is preferably adopted: a water solution of the polysaccharides is prepared; the amino acids or the polycarboxylic acids are added to this water solution, and mixed uniformly and sufficiently; this mixture is heated to be subjected to the crosslinking reaction; and after removing water from the mixture, the mixture is dried, thereby resulting in solids, that is, the water-absorbent resins. When the mixture is dried, it is preferable to set the water to be not more than 5% by weight, that is, to set the water-containing rate of the water-absorbent resins to be not more than 5% by weight. By setting the water-containing rate to not more than 5% by weight, it is possible to obtain water-absorbent resins that have a superior water-absorbing rate under pressure. Here, in order to remove water from the mixture, for example, solid-liquid separating operations such as suction filtration and other operations may be adopted.

The water-absorbent resins, which are obtained through the above-mentioned method, have, for example, fiber-like structures, and are capable of absorbing aqueous liquid (physiologic saline) that is 10 to 50 times as heavy as their own weight. Moreover, under pressure, they are capable of absorbing aqueous liquid that is more than 10 times as heavy as their own weight. Furthermore, the water-absorbent resins are provided with a rate of biodegradability of not less than 10%. In other words, the above-mentioned water-absorbent resins have a water-absorbing rate of not less than 10 g/g with respect to aqueous liquid as well as a rate of biodegradability of not less than 10%. Further, they have a water-absorbing rate of not less than 10 ml/g with respect to aqueous liquid under pressure. Therefore, the water-absorbent resins are superior in both water-absorbent capacity and biodegradability, and are capable of maintaining their water-absorbent capacity under pressure. Additionally, the measuring methods of various performances with respect to the water-absorbent resins will be described in detail in embodiments later.

Moreover, in order to further improve the water-absorbent capacity under pressure of the water-absorbent resins, the water-containing rate may be lowered more by using the following operation: First, the water-absorbent resins which have been obtained through the above-mentioned method, that is, the water-absorbent resins from which the solvent has been removed, are heated for 5 minutes to 1 hour at a temperature of not less than 130° C., more preferably, at a temperature of not less than 150° C. Here, it is not preferable to use a heating temperature of less than 130° C., because the biodegradability of the resulting water-absorbent resins is lowered.

Then, the water-absorbent resins are mixed with demineralized water so as to be swelled to form aqueous gel. The degree of swelling of the aqueous gel is in the order of 10 g/g to 1000 g/g. Next, the aqueous gel is immersed in a great excess of hydrophilic organic solvent so that water contained in the aqueous gel is replaced by the hydrophilic organic solvent. In other words, the aqueous gel is dehydrated. Thereafter, the gel is extracted by the solid-liquid separating operation such as suction filtration, and is dried for a predetermined period of time at a temperature not more than 150° C., thereby resulting in dehydrated water-absorbent resins. As to the hydrophilic organic solvent, ketones such as acetone may be adopted, in addition to the aforementioned lower alcohols.

Additionally, besides the fiber-like structures, the water-absorbent resins may be granulated into a predetermined shape, or may be formed into various shapes, such as an irregular fragment-shape, a globular shape, a scaly shape, a bar shape, and a bulk-shape. Further, the water-absorbent resins may be primary particles, or may be granulated bodies of the primary particles. The method for granulating the water-absorbent resins into a predetermined shape and the diameter of each granulated particle are not especially limited. Moreover, in order to improve the water-absorbing characteristics of the water-absorbent resins, such as the permeability, dispersing property and water-absorbing rate to the aqueous liquid, the water-absorbent resins may be processed or modified in various ways.

The water-absorbent resins that are obtained through the above-mentioned method are used not only as sanitary products in the sanitary field like paper diapers, sanitary napkins, and various cleaning items, but also as products in various fields as described below:

That is, the water-absorbent resins are used as: absorbent materials for body fluids used in surgical operations, protective materials for wounds, and other products in the medical field; sealing materials (water-sealing materials) used in the shield engineering technique, concrete-curing materials, gel water-bag, and anti-dewing materials in the engineering and building fields; drip-absorbing materials and freshness-retaining materials for meat, fish, etc., freshness-retaining materials for vegetables, etc., and other materials in the food field; dehydrating agents for removing water from solvents in the industrial field; and water-retaining materials for soil related to tree-planting or the like, water-retaining materials for plant cultivation, seed-coating materials, and other materials in the gardening and agricultural fields. They are also used for various other products, such as oil-water separating materials, waste-liquid absorbing materials, vibration-proof materials, sound-proof materials, general merchandise for home use, toys, and artificial snow.

Some water-absorbent articles for use in these fields are manufactured by sandwiching the water-absorbent resins with films or other materials having the water-permeability at least on one portion thereof or filling the water-absorbent resins in containers having the water-permeability at least in one portion thereof. Other water-absorbent articles are manufactured by forming the water-absorbent resins into, for example, sheet shapes.

The water-absorbent articles using the water-absorbent resins have biodegradability such that they are decomposed by bacteria, microbes, etc., in the ground; this makes it possible to dispose of these articles merely by burying them in the ground. Thus, they make it possible to simplify the waste-disposal process, are capable of improving safety, and do not cause any problems in environment hygiene, such as environmental contaminations. Therefore, the water-absorbent articles may be applied to all the usages of the conventionally known water-absorbent articles.

Among the above-mentioned fields, the water-absorbent articles, that is, the water-absorbent resins, are preferably used in the hygiene field, medical field, and food field because they are especially superior in biodegradability and safety. Additionally, the compositions of the water-absorbent resins (that is, kinds of the polysaccharides, amino acids, polycarboxylic acids, etc.) may be preferably selected so as to obtain performances suitable for each specific usage among the above-mentioned usages.

Moreover, in order to improve their processability and their quality and performance, for example, the following agents and materials are added to the water-absorbent articles, as occasion demands: fillers made of inorganic fine particles, such as silica fine particles, and pulp fibers or the like; deodorants or deodorizers mainly constituted of zeolite or other materials whereto activated charcoal and ferrophthalocyanine derivatives, vegetative essential oil, etc. are adsorbed; aromatics; anti-fungus agents mainly constituted of metals, such as silver, copper and zinc, and other materials; bactericides; mildewproofing agents; antiseptic agents; deoxidizing agents (antioxidants); surfactants; gas-developing agents; and perfumes. Various functions may be imparted to the water-absorbent articles by adding some of these additives thereto. The amounts of addition of these additives, which vary depending on the kinds of the additives, may be mainly set within the range of 0.01% to 5% by weight with respect to the water-absorbent resins. Here, the methods for adding the additives are not especially limited.

DESCRIPTION OF THE EMBODIMENTS

The following description will discuss the present invention in detail with reference to embodiments and comparative examples. However, the present invention is not intended to be limited thereby. Here, the various performances of the water-absorbent resins are measured through the following methods. In addition, "part" used in the embodiments and comparative examples refers to "part by weight".

(a) Water-absorbing ratio:

0.2 grams of the water-absorbent resins is uniformly put into a bag like a tea-bag (40 mm×150 mm) made of nonwoven cloth, and is immersed into a solution of sodium chloride of 0.9% by weight (physiologic saline). 60 minutes later, the bag is taken out, and after being subjected to hydro-extraction for a predetermined period of time, the weight $W_1(g)$ of the bag is measured. Further, the same processes are carried out without using the water-absorbent resins, and the weight $W_0$ (g) of the bag is measured. The water-absorbing ratio (g/g) is calculated from the weights $W_1$ and $W_0$ in accordance with the following equation:

Water-absorbing ratio (g/g)=(Weight $W_1(g)$−Weight $W_0(g)$)/Weight of Water-absorbent resins (g).

Figure 1:
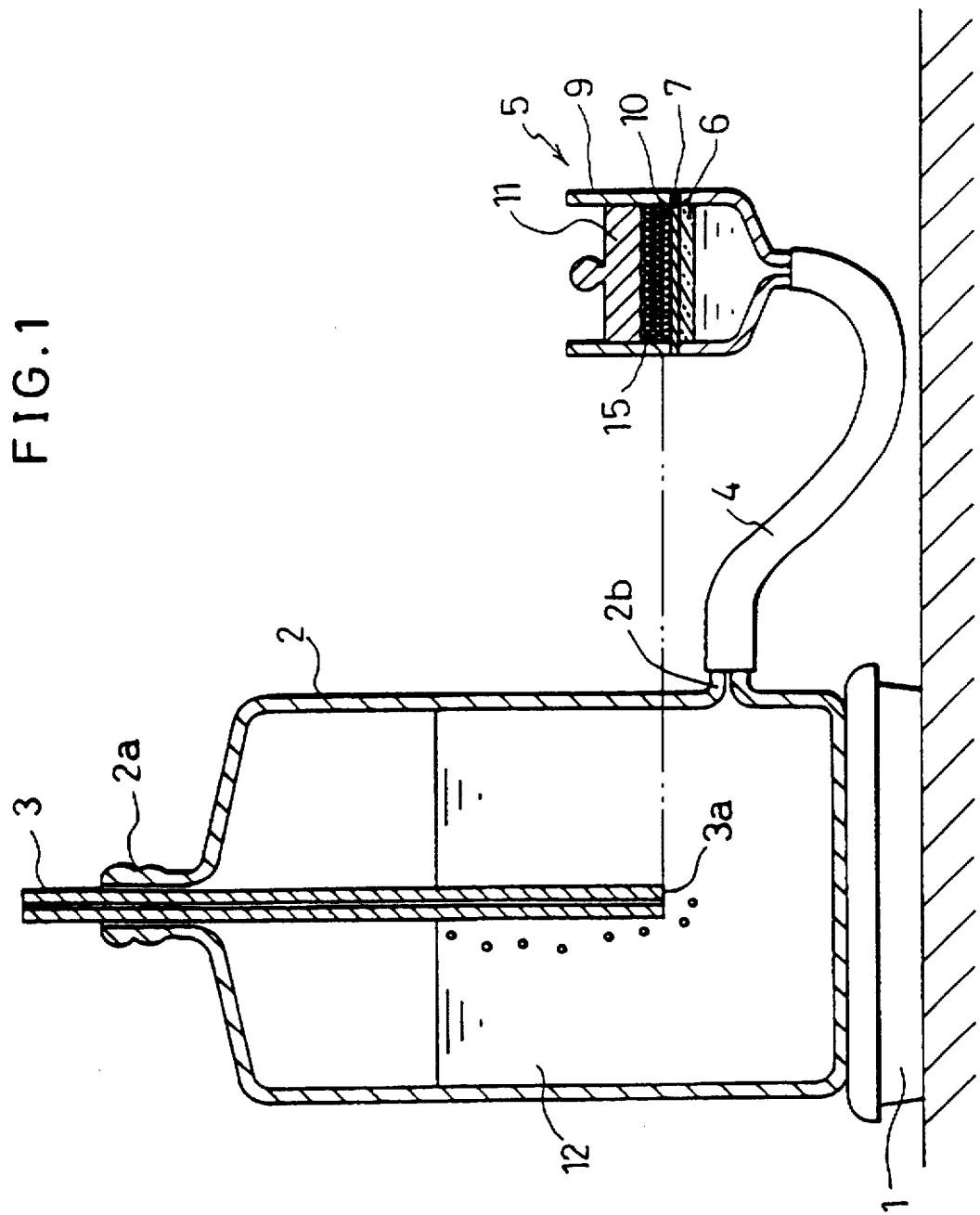
FIG. 1 is a schematic vertical sectional view showing a measuring device for measuring the water-absorbing rate under pressure that is one of the performances of water-absorbent resins in the present invention.

(b) Water-absorbing ratio under pressure:

First, the following description will briefly discuss a measuring device for use in measurements of the water-absorbing ratio under pressure with reference to FIG. 1.

As shown in FIG. 1, the measuring device is constituted by a weighing machine 1, a container 2 placed on the weighing machine 1 with a predetermined capacity, an air-intake pipe 3, a conduit 4, a glass filter 6, and a measuring section 5 that is placed on the glass filter 6. The container 2 has an opening 2a at its top and an opening 2b at its side, and the air-intake pipe 3 is inserted through the opening 2a while the conduit 4 is fixed to the opening 2b. Further, the container 2 contains a predetermined amount of physiologic saline 12. The lower end of the air-intake pipe 3 is located in the physiologic saline 12. The air-intake pipe 3 is provided so as to maintain the pressure inside the container 2 at atmospheric pressure. The glass filter 6 has a diameter of 55 mm. The container 2 and the glass filter 6 are connected to each other through the conduit 4 made of silicone resin. The glass filter 6 is fixed at a predetermined position and level with respect to the container 2.

The measuring section 5 is provided with a paper filter 7, a supporting cylinder 9, a metal gauze 10 that is affixed to the bottom of the supporting cylinder 9, and a weight 11. In the measuring section 5, the paper filter 7, the supporting cylinder 9 (that is, the metal gauze 10) are placed on the glass filter 6 in this order, and the weight 11 is placed on the metal gauze 10 inside the supporting cylinder 9. The metal gauze 10, made of stainless steel, is designed to have 400 meshes (the size of each mesh: 38 μm). Moreover, the metal gauze 10 is disposed so that the upper surface thereof, that is, the contact face between the metal gauze 10 and the water-absorbent resins 15, is aligned as high as the lower-end face 3a of the air-intake pipe 3. Thus, the water-absorbent resins 15 having a predetermined amount and a predetermined particle-diameter are uniformly scattered on the metal gauze 10. The weight 11 is adjusted so that it can uniformly apply a load of 15.7 g/cm² to the metal gauze 10, that is, to the water-absorbent resins 15.

The water-absorbing ratio under pressure is measured by using the measuring device having the above-mentioned arrangement. The following description will discuss the measuring method.

First, predetermined preparatory operations are carried out, wherein a predetermined amount of physiologic saline 12 is put into the container 2; the air-intake pipe 3 is inserted into the container 2; and other operations are executed. Next, the paper filter 7 is placed onto the glass filter 6. Further, during this placing-process, 0.2 grams of the water-absorbent resins is uniformly scattered on the metal gauze 10 inside the supporting cylinder 9, and the weight 11 is placed on the water-absorbent resins 15.

Successively, the metal gauze 10, that is, the supporting cylinder 9 whereon the water-absorbent resins 15 and the weight 11 have been placed, is placed on the paper filter 7, with its center coinciding with the center of the glass filter 6.

Then, the volume $V_1$(ml) of the physiologic saline 12, which has been absorbed by the water-absorbent resins 15 for 60 minutes from the time when the supporting cylinder 9 was placed on the paper filter 7, is found by converting the measurements of the weighing machine 1. Further, the same processes are carried out without using the water-absorbent resins 15, and the blank weight, that is, the volume $V_0$(ml) of the physiologic saline 12, which has been absorbed by, for example, the paper filter 7 and other materials except the water-absorbent resins 15, is found by converting the measurements of the weighing machine 1.

The water-absorbing ratio under pressure (ml/g) is calculated from the volumes $V_1$, and $V_0$ in accordance with the following equation:

Water-absorbing ratio under pressure (ml/g)=(Volume $V_1$(ml)−Volume $V_0$(ml)) / Weight of Water absorbent resins (g).

(c) Rate of Biodegradability:

The test of biodegradation is carried out in accordance with the corrected MITI(Ministry of International Trade and Industry) test. More specifically, 200 ml of a basic culture solution is prepared as tissue liquid that is standardized in the item of biochemical oxygen demand in JIS K-0102. To this is added the water-absorbent resins as a test substance so as to make 100 ppm, as well as adding active sludge thereto so as to make 30 ppm. Then, the basic culture solution is maintained at 25° C. in a dark room, and cultured for 28 days while being stirred. During the culturing period, the amount of oxygen, which have been consumed by the active sludge, is periodically measured so as to find a curb of BOD (Biochemical Oxygen Demand).

The rate of biodegradability(%) is calculated from the biochemical oxygen demand A(mg) of the test substance (water-absorbent resins) obtained from the BOD curb, the blank that is obtained from the BOD curb, that is, the amount of oxygen consumption of the basic culture solution B(mg), and the total oxygen demand (TOD) C(mg) that is required for completely oxidizing the test substance, in accordance with the following equation:

Rate of biodegradability(%)={$(A-B)/C$}×100.

(d) Amount of Water Retention:

The bag like tea-bag, which has been subjected to the measurements related to the water-absorbing ratio, that is, the bag containing the swollen water-absorbent resins, is set in a centrifugal separator, and centrifuged at 1500 rpm (centrifugal force: 200 G) for 10 minutes so as to be dewatered. Thereafter, the bag is taken out, and the weight $W_3(g)$ of the bag is measured. Further, the same processes are carried out without using the water-absorbent resins, and the weight $W_2(g)$ of the resulting bag is measured. Then, the amount of water retention is calculated from the weights $W_3$ and $W_2$, in accordance with the following equation:

Amount of water retention(g/g)=(Weight $W_3(g)$−Weight $W_2(g)$)/ Weight of water-absorbent resins (g).

EMBODIMENT 1

480 parts of distilled water is prepared as a solvent. 20 parts of carboxymethylcellulose (brand name: aquasorb B313 manufactured by Aqualon Co., Ltd.), prepared as one of the polysaccharides, is dissolved in the solvent to form 500 parts of water solution of carboxymethylcellulose (4% by weight). Further, 99.9 parts of distilled water is prepared as a solvent. 0.1 part of aspartic acid, prepared as one of the amino acids, is dissolved in the solvent to form 100 parts of water solution of aspartic acid (0.1% by weight).

Next, the water solution of aspartic acid is mixed with the water solution of carboxymethylcellulose, and stirred sufficiently. Successively, the resulting mixture is dried by heating it at 120° C. for 70 minutes by the use of a dryer, thereby obtaining a dried substance. The dried substance is ground by a vibration mill to form a water-absorbent resin. The water-absorbent resin thus obtained is measured on its water-absorbing ratio, water-absorbing ratio under pressure, and rate of biodegradability (hereinafter, referred to as various performances). These values (hereinafter, referred to simply as results) are shown in Table 1 collectively.

EMBODIMENT 2

The same reactions and operations as those in Embodiment 1 are carried out except that the heating time, which has been 70 minutes in Embodiment 1, is changed to 160 minutes, and a water-absorbent resin is obtained. The water-absorbent resin thus obtained is measured on its various performances, and the results are shown in Table 1 collectively. Here, the water-absorbent resin obtained in Embodiment 2 is superior in its gel strength to the water-absorbent resin of Embodiment 1.

EMBODIMENT 3

The same reactions and operations as those in Embodiment 1 are carried out except that 0.1 part of polyaspartic acid is used as one of the amino acids instead of 0.1 part of the aspartic acid as well as using the heating time of 90 minutes instead of 70 minutes, and a water-absorbent resin is obtained. The water-absorbent resin thus obtained is measured on its various performances, and the results are shown in Table 1 collectively.

EMBODIMENT 4

The same reactions and operations as those in Embodiment 3 are carried out except that the use of polyaspartic acid is changed from 0.1 part of Embodiment 1 to 1.0 part as well as changing the heating time from 70 minutes to 30 minutes, and a water-absorbent resin is obtained. The water-absorbent resin thus obtained is measured on its various performances, and the results are shown in Table 1 collectively.

EMBODIMENT 5

The same reactions and operations as those in Embodiment 3 are carried out except that the heating time is changed from 90 minutes of Embodiment 3 to 160 minutes, and a water-absorbent resin is obtained. The water-absorbent resin thus obtained is measured on its various performances, and the results are shown in Table 1 collectively.

EMBODIMENT 6

The same reactions and operations as those in Embodiment 3 are carried out except that the heating temperature is changed from 120° C. of Embodiment 3 to 150° C. as well as changing the heating time from 90 minutes to 20 minutes, and a water-absorbent resin is obtained. The water-absorbent resin thus obtained is measured on its various performances, and the results are shown in Table 1 collectively.

EMBODIMENT 7

The same reactions and operations as those in Embodiment 1 are carried out except that 20 parts of starch-glycolic acid (brand name: primogel manufactured by Matsutani Chemical Co., Ltd.) is used as one of the polysaccharides instead of 20 parts of carboxymethyl-cellulose in Embodiment 1, and a water-absorbent resin is obtained. The water-absorbent resin thus obtained is measured on its various performances, and the results were shown in Table 1 collectively.

EMBODIMENT 8

The same reactions and operations as those in Embodiment 7 are carried out except that 0.1 part of polyaspartic acid is used as one of the amino acids instead of 0.1 part of aspartic acid in Embodiment 7 and a water-absorbent resin is obtained. The water-absorbent resin thus obtained is measured on its various performances, and the results are shown in Table 1 collectively.

EMBODIMENT 9

Into a reaction vessel having a stirring mill, are supplied the following materials: 83 grams of isopropyl alcohol used as a solvent; 4 grams of ground conifer craft pulp; and 20 grams of sodium hydroxide solution (15% by weight). This mixture is stirred for one hour at 30° C. Next, to this mixture is added a solution containing 2 grams of isopropyl alcohol and 2 grams of chloroacetic acid (etherifying agent), while taking it into consideration not to raise the temperature of the mixture (reaction system). After the addition, the mixture is stirred for 30 minutes at 30° C., the temperature of the mixture is raised from 30° C. to 74° C. gradually in 30 minutes, and the mixture is further stirred for one hour at 74° C. Thus, a mixed solution of isopropyl alcohol and water, which contains a sufficient amount of carboxymethylcellulose sodium salt (salts of polysaccharides) having a degree of etherification of 0.4, is prepared.

Next, to this mixed solution is added 4.1 grams of aspartic acid prepared as one of the amino acids. After stirring the mixed solution sufficiently at 74° C., isopropyl alcohol and water (filtrate) are removed therefrom by suction-filtrating the mixed solution, thereby obtaining a reaction product (cake). Then, the reaction product is washed with 200 ml of methyl alcohol water-solution (60 vol%) two times, and again with 200 ml of methyl alcohol one time. After the washing, the reaction product is subjected to a heating treatment for 15 minutes at 150° C. by the use of a hot-air dryer, thereby resulting in a crosslinked carboxymethylcellulose salt.

Successively, 1 gram of the crosslinked carboxymethylcellulose salt is mixed with 50 grams of demineralized water to form an aqueous gel. The aqueous gel is immersed in a great excess of methyl alcohol prepared as a hydrophilic organic solvent, and water contained in the aqueous gel is replaced by methyl alcohol. In other words, the aqueous gel is dehydrated. Thereafter, the aqueous gel is suction-filtrated, thereby resulting in a solid matter (gel).

The solid matter is dried under vacuum for one hour at 50° C. by using a hot-air dryer, thereby obtaining a water-absorbent resin. The water-absorbent resin thus obtained is measured on its various performances, and the results are shown in Table 1 collectively.

COMPARATIVE EXAMPLE 1

A 2-liter 4-neck round-bottom flask, which has an agitator, a reflux condenser, a dropping funnel and a nitrogen-gas blowing tube, is prepared as a reaction vessel. 1150 ml of cyclohexane and 9.0 grams of ethylcellulose (brand name: ethylcellulose N-200, manufactured by Hercules Co., Ltd.) are loaded in this reaction vessel. Next, into this is blown nitrogen gas so as to remove dissolved oxygen, and then the solution is heated to 75° C.

On the other hand, 65.8 grams of sodium hydroxide (98% by weight) is dissolved in 200 grams of ion exchange water so as to prepare a water solution of sodium hydroxide. Then, 150 grams of acrylic acid, which is loaded in another flask, is neutralized by using the water solution of sodium hydroxide. The concentration of the water solution of sodium polyacrylate is 45 wt%. To this are added and dissolved 0.5 grams of potassium persulfate and 0.15 grams of N,N'-methylene-bis acrylamide as polymerization initiators. Here, the rate of the initiator to the acrylic acid is 0.1 wt %. Then, nitrogen gas is blown into the solution so as to remove oxygen therefrom. This water solution is put into the dropping funnel, and dropped into the 4-neck flask gradually in one hour. After completion of the dropping, the reaction is continued for one hour while maintaining at 75° C. After completion of the reaction, cyclohexane is removed therefrom through distilling under vacuum, and the remaining swollen polymer is dried under vacuum at 80°-100° C., thereby obtaining a water-absorbent resin for comparative use. The water-absorbent resin thus obtained is measured on its various performances, and the results are shown in Table 1 collectively.

COMPARATIVE EXAMPLE 2

50 parts of corn starch and 300 parts of water are loaded into a reaction vessel that is provided with an agitator, a thermometer, and a nitrogen-gas blowing tube. This mixture is stirred for one hour at 50° C. while blowing nitrogen gas thereto. Successively, after cooling the mixture to 30° C., to this are added 20 parts of acrylic acid, 80 parts of sodium acrylate, and 0.02 parts of N,N'-methylene-bis acrylamide together with 0.1 part of sodium persulfate and 0.01 part of sodium hydrogensulfite as polymerization initiators, thereby initiating a polymerization reaction. After the reaction has been carried out for four hours at reaction temperatures of 30° C. to 80° C., a water-containing gel polymer is obtained.

The water-containing gel polymer thus obtained is dried by hot air at 120° C. Next, the dried matter is ground, thereby obtaining a water-absorbent resin for comparative use, which is made of starch graft polymer. The water-absorbent resin for comparative use thus obtained is measured on its various performances, and the results are shown in Table 1 collectively.

EMBODIMENT 10

Into a reaction vessel having a stirring mill, are supplied the following materials: 83 grams of isopropyl alcohol used as a solvent; 4 grams of ground conifer craft pulp; and 20 grams of sodium hydroxide solution (15% by weight). This mixture is stirred for one hour at 30° C. Next, to this mixture is added a solution containing 2 grams of isopropyl alcohol and 2 grams of chloroacetic acid (etherifying agent), while taking it into consideration not to raise the temperature of the mixture (reaction system). After the addition, the mixture is stirred for 30 minutes at 30° C., the temperature of the mixture is raised from 30° C. to 74° C. gradually in 30 minutes, and the mixture is further stirred for one hour at 74° C. Thus, a mixed solution of isopropyl alcohol and water, which contains a sufficient amount of carboxymethylcellulose sodium salt (salts of polysaccharides) having a degree of etherification of 0.4, is prepared.

Next, to this mixed solution is added 2 grams of citrate as one of the polycarboxylic acids. After stirring the mixed solution sufficiently at 74° C., isopropyl alcohol and water (filtrate) are removed therefrom by suction-filtrating the mixed solution, thereby obtaining a reaction product (cake). Then, the reaction product is washed with 200 ml of methyl alcohol water-solution (60 vol %) two times, and again with 200 ml of methyl alcohol one time. After the washing, the reaction product is subjected to a heating treatment for 30 minutes at 150° C. by the use of a hot-air dryer, thereby resulting in a crosslinked carboxymethylcellulose salt.

Successively, 1 gram of the crosslinked carboxymethylcellulose salt is mixed with 50 grams of demineralized water to form an aqueous gel. The aqueous gel is immersed in a great excess of methyl alcohol prepared as a hydrophilic organic solvent, and water contained in the aqueous gel is replaced by methyl alcohol. In other words, the aqueous gel is dehydrated. Thereafter, the aqueous gel is suction-filtrated, thereby resulting in a solid matter (gel).

The solid matter is dried under vacuum for one hour at 120° C. by using a hot-air dryer, thereby obtaining a water-absorbent resin. The water-absorbent resin thus obtained is measured on its various performances, and the results are shown in Table 2 collectively. Here, the water-absorbing ratio (g/g) is the value obtained when the water-absorbent resin is immersed in physiologic saline for 5 minutes.

TABLE 1

|  | Water-Absorbing Ratio (g/g) | Water-Absorbing Ratio under Pressure (g/ml) | Rate of Biodegradability (%) |
| --- | --- | --- | --- |
| Embodi. | | | |
| 1 | 26.0 | 24.0 | 13.0 |
| 2 | 18.6 | 22.5 | 24.2 |
| 3 | 24.9 | 20.5 | 29.7 |
| 4 | 21.8 | 11.5 | 12.2 |
| 5 | 16.6 | 18.5 | 16.1 |
| 6 | 24.0 | 17.5 | 16.0 |
| 7 | 11.3 | 10.5 | 46.7 |
| 8 | 12.7 | 11.0 | 47.2 |
| 9 | 22.4 | 12.5 | 60.0 |
| Com. Exa. | | | |
| 1 | 58.0 | 13.0 | 0.0 |
| 2 | 60.0 | 16.3 | 2.0 |

TABLE 2

|  | Water-Absorbing Ratio (g/g) | Rate of Water Retention (g/g) | Rate of Biodegradability (%) |
| --- | --- | --- | --- |
| Embodi. 10 | 17.0 | 13.0 | 65.0 |

As clearly shown by the results of Embodiments 1 through 10 as well as Comparative Examples 1 and 2, the water-absorbent resins in accordance with the present invention are superior in both their water-absorbing capacity and biodegradability, and are capable of maintaining their water-absorbing capacity even under pressure, in comparison with conventional water-absorbent resins.

EMBODIMENT 11

By using the water-absorbent resin that have been obtained through the same reactions and operations as those shown in Embodiment 1, paper diapers, which are one type of the water-absorbent products, are manufactured by a method as will be described below.

First, 8 grams of the water-absorbent resin and 30 grams of ground pulp are mixed by a mixer in a dry state. Next, the resulting mixture is webbed on a wire screen having a predetermined meshes by using a batch-type air-laying device so that a web having a size of 14 cm×40 cm, is formed. After sandwiching the web with sheets of tissue paper on its upper and lower surfaces, it is embossed for one minute at 150° C. under a predetermined pressure so as to form a water-absorbent material. Here, the tissue paper has a basis weight of 0.0013 g/cm².

Figure 2:
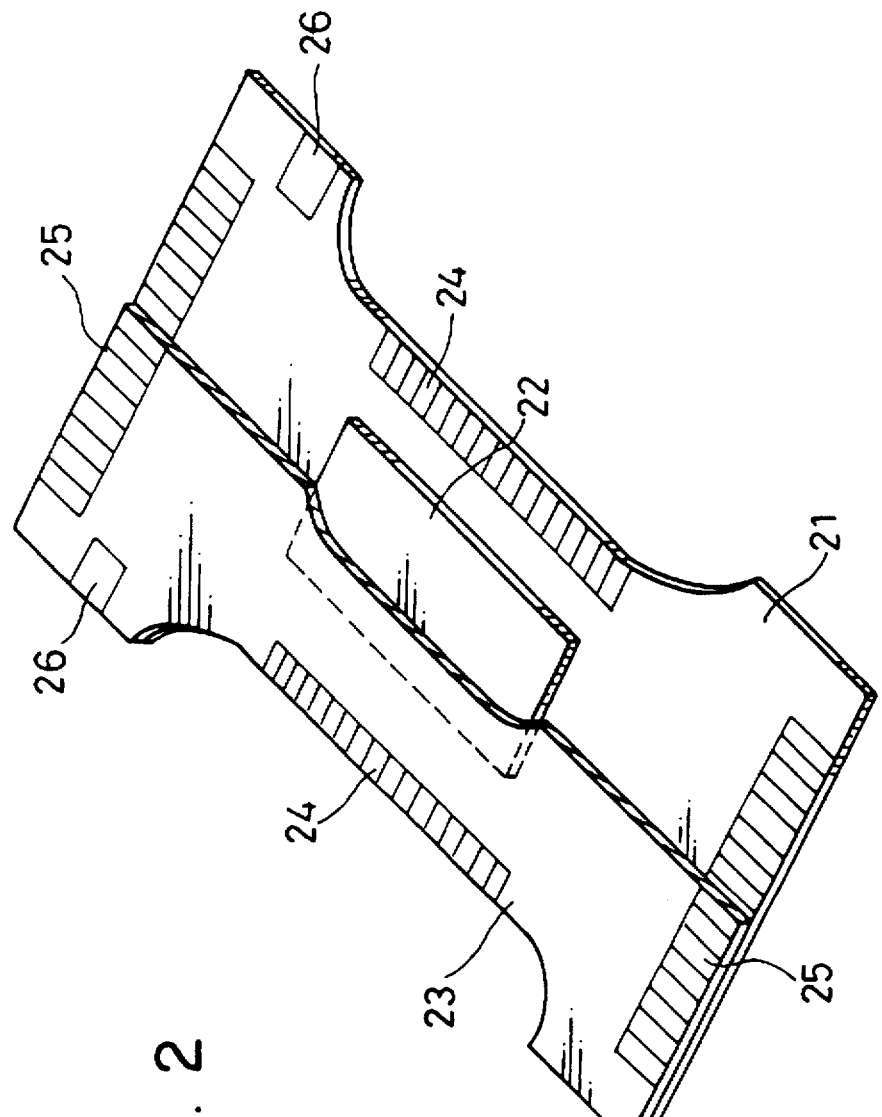
FIG. 2 is a partially exploded perspective view that schematically shows one portion of a paper diaper that is one of the water-absorbent articles using the water-absorbent resins of the present invention.

Successively, as shown in FIG. 2, a backsheet 21, the water-absorbent material 22 and a topsheet 23 are bonded to one another with double-sided tapes in this order. The backsheet 21, made of non-liquid-permeable polyethylene, has been cut into a predetermined shape. The topsheet 23, made of liquid-permeable polypropylene, has been cut into virtually the same shape as the backsheet 21. Then, so-called leg gathering 24 and waist gathering 25 are provided at predetermined positions on the bonded article. Further, so-called tape fasteners 26 are fixed to predetermined positions on the bonded article. Thus, a paper diaper, which is one type of the water-absorbent articles, is manufactured. The weight of the paper diaper is approximately 54 grams.

In order to evaluate paper diapers having the above structure, a group of ten babies went through a set of thirty diapers each. The results proved that the diapers were well-suited for preventing leakage or other problems. Further, the paper diapers are superior in biodegradability compared with conventional paper diapers.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A water-absorbent resin prepared by having at least one kind of polysaccharide crosslinked by at least one kind of amino acid.

2. The water-absorbent resin as set forth in claim 1, wherein the polysaccharide is at least one kind selected from the group consisting of carboxyalkylcellulose, carboxyalkylstarch, and salts thereof.

3. The water-absorbent resin as set forth in claim 1, wherein the amino acid is at least one kind selected from the group consisting of amino acids and amino acid polymers.

4. The water-absorbent resin as set forth in claim 1, wherein the amino acid is at least one kind of acidic amino acid.

5. A water-absorbent resin having a water-absorbing ratio of not less than 10 g/g with respect to physiologic saline, a water-absorbing ratio under pressure of not less than 10 ml/g with respect to physiologic saline, and a rate of biodegradability of not less than 10%.

6. The water-absorbent resin as set forth in claim 1, wherein the polysaccharide is carboxymethylcellulose and the amino acid is at least one member selected from the group consisting of aspartic acid and polyaspartic acid.

7. The water-absorbent resin as set forth in claim 1, wherein the polysaccharide is starch-glycolic acid and the amino acid is at least one member selected from the group consisting of aspartic acid and polyaspartic acid.

8. The water-absorbent resin as set forth in claim 5, wherein the water-absorbent resin is in particulate form.

* * * * *